United States Patent [19]
Tsukada et al.

[11] Patent Number: 5,352,352
[45] Date of Patent: Oct. 4, 1994

[54] CARBONIC ACID GAS SENSOR

[75] Inventors: Keiji Tsukada, Chiba; Yuji Miyahara, Hitachi; Yasuhisa Shibata, Ibaraki; Yoshio Watanabe, Kokubunji, all of Japan

[73] Assignee: Hitachi, Ltd., Tokyo, Japan

[21] Appl. No.: 948,646

[22] Filed: Sep. 23, 1992

[30] Foreign Application Priority Data

Sep. 24, 1991 [JP] Japan .................. 3-243516

[51] Int. Cl.⁵ .......................................... G01N 27/404
[52] U.S. Cl. ................. 204/415; 204/153.22; 204/414; 204/419; 204/433
[58] Field of Search .................. 204/415–420, 204/153.17, 153.22, 433

[56] References Cited

U.S. PATENT DOCUMENTS

| | | | |
|---|---|---|---|
| 4,474,648 | 10/1984 | Tantram et al. | 204/415 |
| 4,505,807 | 3/1985 | Yamada | 204/425 |
| 4,536,274 | 8/1985 | Papadakis et al. | 204/415 |
| 4,578,154 | 3/1986 | Kitamura et al. | 204/415 |
| 4,613,422 | 9/1986 | Lauks | 204/416 |
| 4,790,925 | 12/1988 | Miller et al. | 204/415 |
| 4,824,551 | 4/1989 | Rupich | 204/415 |
| 4,842,712 | 6/1989 | Seshimoto et al. | 204/416 |
| 4,874,499 | 10/1989 | Smith et al. | 204/416 |
| 4,938,860 | 7/1990 | Wogoman | 204/415 |
| 4,950,379 | 8/1990 | Young et al. | 204/403 |
| 4,975,175 | 12/1990 | Karube et al. | 204/415 |
| 5,102,525 | 4/1992 | Miyahara et al. | 204/415 |
| 5,120,420 | 6/1992 | Nankai et al. | 204/415 |
| 5,138,251 | 8/1992 | Koshiishi et al. | 204/416 |
| 5,183,550 | 2/1993 | Mattiessen | 204/415 |

FOREIGN PATENT DOCUMENTS

| | | |
|---|---|---|
| 284518 | 9/1988 | European Pat. Off. |
| 61-88138 | 5/1986 | Japan |
| 63-26569 | 2/1988 | Japan |
| 63-279154 | 11/1988 | Japan |

OTHER PUBLICATIONS

Suzuki et al, Analytica Chimica Acta, "Effect of Anode Materials on the Characteristics of the Miniature Clark-type Oxygen Electrode", vol. 233, pp. 275–280, 1990.
B. Hagiwara, "Oxygen Measurement by the Electrode Method", pp. 11–12.
Sensors and Actuators, vol. B, No. 2, 1990, "An Integrated Chemical Sensor with Multiple Ion and Gas Sensors", K. Tsukada et al, pp. 291–295.

*Primary Examiner*—T. Tung
*Attorney, Agent, or Firm*—Fay, Sharpe, Beall, Fagan, Minnich & McKee

[57] ABSTRACT

A sensor for detecting a carbonic acid gas dissolved in body fluids has a laminated structure including an outer plate having a carbonic acid gas permeable window, a plate for a pH-electrode having a pH sensitive membrane, an intermediate plate having a cavity for accommodating an electrolyte, and a plate for a reference electrode. The plate for the pH-electrode is constituted in a manner that a pH sensitive membrane constituted by a membrane of an oxide of a platinum group metal is formed on an insulating substrate and the electrolyte contacts with the pH sensitive membrane in a groove. The pH sensitive membrane is disposed so as to oppose to the carbonic acid gas permeable window.

12 Claims, 4 Drawing Sheets

CARBONIC ACID GAS SENSOR

BACKGROUND OF THE INVENTION

The present invention generally relates to carbonic acid gas sensors and, more particularly, is directed to a sensor used for measuring a carbonic acid gas dissolved in a body fluid or a fluid such as water in a river.

A Severinghaus-type carbonic acid gas sensor has been most popularly employed as a carbonic acid gas sensor for measuring a carbonic acid gas dissolved in a fluid. The Severinghaus-type carbonic acid gas sensor is described, for example, in "Theory of Measurement of a Blood Gas and Clinical Application thereof" by Takanori Fujiwara, Shinkou Koueki Medical Book Publishing Section, pp. 150 to 152.

In the Severinghaus-type carbonic acid gas sensor, a gas permeable membrane of tetrafluoroethylene, for example, is attached at a tip portion of a sensor body, and an electrolyte solution including sodium bicarbonate is filled in the sensor body. Further, the sensor employs a pH-electrode having an internal electrolyte solution and employs a glass membrane as a pH sensitive membrane for the pH-electrode. The pH-electrode is mounted in the sensor so as to closely contact with the gas permeable membrane through the electrolyte solution. In the thus-constituted sensor, when the sensor contacts with a solution to be measured, a carbonic acid gas is diffused into the electrolyte solution including sodium bicarbonate through the gas permeable membrane and dissolves in the solution, so that the pH of the electrolyte solution changes. This change of pH can be detected by the pH-electrode provided in the sensor. According to this theory, the partial pressure of the carbonic acid gas in the solution can be measured.

A carbonic acid gas sensor which is fabricated by miniaturizing the Severinghaus-type carbonic acid gas sensor on the basis of semiconductor manufacturing techniques is described in "Proceeding of the Symposium on Biosensors" 1984, pp. 33 to 34. This carbonic acid gas sensor employs, instead of the pH-electrode of the above-described sensor, an ion-sensitive field effect transistor (ISFET) which is an all solid type sensor having no internal electrolyte solution. In this carbonic acid gas sensor, the ISFET is disposed in a catheter tube, an electrolyte gel is filled on a pH sensitive membrane which is a gate of the ISFET and then the gel is covered by a gas permeable membrane.

Another example of a carbonic acid gas sensor, in which a gas permeable membrane and an electrolyte gel as well as a pH-electrode are embedded by utilizing semi-conductor manufacturing techniques is described in "Sensors and Actuators B2", 1990, pp. 291 to 295. In this carbonic acid gas sensor, a pressure membrane of polyimide is coated on a sensor substrate, and a groove is formed on a gate of an ISFET. Then, an electrolyte gel is filled in the groove, thereby forming a gas permeable membrane.

The firstly-described conventional Severinghaus-type carbonic acid gas sensor is a sensor of a type assembled on the basis of mechanical structure, and so has a life time of more than one year as long as it is not used in an inferior environment, and therefore has a high reliability. However, since each of the parts constituting the Severinghaus-type sensor is fabricated by mechanical processes, there have been problems difficult to be overcome in automatization of assembling processes and improvement of mass productivity that have been difficult to overcome.

In the secondly-described conventional carbonic acid gas sensor fabricated on the basis of the semiconductor manufacturing techniques, the ISFET serving as a pH-electrode has a high mass productivity. However, since all elements of the sensor including the pH-electrode, tube and gas permeable window or the like have not been embedded yet, there has been a problem in automization of assembling processes of the sensor and mass productivity. Further, since, after filling of the electrolyte gel on the pH sensitive membrane, the electrolyte gel is covered by the gas permeable membrane, there has been a problem that a distance between the gas permeable membrane and a pH sensitive portion of the ISFET is determined in accordance with an amount of the filled electrolyte. The response time of the sensor is influenced by this distance, so that the response time fluctuates greatly depending on the amount of the filled electrolyte.

In the thirdly-described conventional carbonic acid Gas sensor in which the Gas permeable membrane is embedded on a semiconductor substrate, an amount or capacity of the electrolyte gel is determined by the capacity of a groove formed on the gate of the ISFET. Since an area of the gate of the ISFET is small, the groove is required to be deeper in order to increase a capacity of the electrolyte gel. However, the deeper the groove is, the lower the response speed of the sensor becomes, so that the capacity of the electrolyte gel is limited. Thus, there has been a problem that the life time of the sensor is short.

As other related prior art, there have been known Japanese Patent Laid Open Publication Nos. (JP-As) 61-88138, 63-26569 and 63-279154.

JP-A 61-88138 discloses an electrochemical apparatus which has a laminated structure of a sheet-shaped solid electrolyte and a sheet-shaped electrode disposed in contact with the solid electrolyte.

JP-A 63-26569 discloses an ion selective electrode apparatus in which a path for the medium to be measured is provided, an electrolyte solution such as human blood is flown through the path, and then an ion concentration of the electrolyte solution is measured by utilizing a reference electrode and an indicator electrode disposed in a mutually insulated state.

JP-A 63-279154 discloses a sensor for detecting carbon dioxide which is constituted in a manner that recesses are formed on the entire surface of a semiconductor substrate, an agarose gel including an electrolyte solution is filled in the recesses, and then the recesses are covered by a gas permeable membrane.

SUMMARY OF THE INVENTION

An object of the present invention is to provide a carbonic acid gas sensor having a laminated structure that is suitable for mass production.

According to one aspect of the present invention, a carbonic acid gas sensor includes an outer plate having a carbonic acid gas permeable window, a plate for a pH-electrode for detecting pH, and a plate for a reference electrode. These three plates are laminated, and the plate for the pH-electrode includes an insulating substrate, a pH sensitive membrane formed on the substrate, and a compartment for accommodating an electrolyte. The pH sensitive membrane of the plate for the pH-electrode is disposed opposite to the carbonic acid gas permeable window.

According to a preferred embodiment of the present invention, the pH sensitive membrane is constituted of a layer formed by an indium oxide or an oxide of platinum group metal selected from the group consisting of a palladium oxide, an iridium oxide and a platinum oxide. The plate for the pH-electrode disposed adjacent to the outer plate includes a conductive layer formed on a flat substrate and connected to an external lead wire, and the pH sensitive membrane is disposed on the conductive layer so as to cover a part thereof. Each of the plate for the pH-electrode and the plate for the reference electrode has a through hole for wiring, and the lead wire connected to the conductive layer is extracted out of the plate for the reference electrode through the through holes. The pH sensitive membrane contacts with the electrolyte in the compartment. The compartment includes a hole formed in the substrate and a groove formed at a part of a composite resin layer covering the surface of the substrate, and the groove communicates with the hole. The area of the pH sensitive membrane is smaller than the area of the carbonic acid gas permeable window.

The preceding and other objects, features, and advantages of the present invention will become apparent from the following detailed description of illustrative embodiment thereof when read in conjunction with the accompanying drawings, in which like reference numerals are used to identify the same or similar parts in the several views.

DETAILED DESCRIPTION OF THE PREFERRED EMBODIMENT

Figure 1:
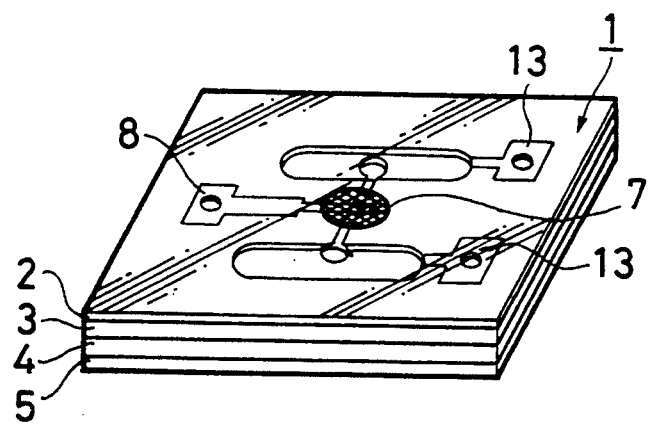
FIG. 1 is a schematic perspective view illustrating a carbonic acid gas sensor according to an embodiment of the present invention.

A principle of a carbonic acid gas sensor according to the present invention Will be explained prior to the explanation of specific embodiment of the present invention.

The carbonic acid gas sensor according to the present invention is able to measure the partial pressure of a carbonic acid gas dissolved in body fluids or fluids such as water in a river.

To this end, an outer plate of the sensor has a carbonic acid gas permeable window which is formed by covering a through hole provided in a substrate of the outer plate with a carbonic acid gas permeable membrane.

A plate for a pH-electrode adjacent to the outer plate is formed by providing a pH-electrode on a flat insulating substrate. The pH-electrode has a conductive layer formed by a patterning process and connectable to a lead wire for extracting a pH detection signal, a pH sensitive membrane disposed to cover a part of the conductive layer, and an electrolyte contacting with the pH sensitive membrane. A major part of the surface of the plate for the pH-electrode is covered by a synthetic resin layer. The synthetic resin layer has a function of forming a compartment for accommodating the electrolyte. The compartment has a through hole formed in the substrate of the plate for the pH-electrode, and a groove formed by the synthetic resin layer. The electrolyte is used in a state of solution or gel.

In a plate for a reference electrode adjacent to the plate for the pH-electrode, a silver/chloride electrode is formed on an insulating substrate. The surface of each of the plates for the pH-electrode and the reference electrode is covered by an insulating layer of synthetic resin, for example. These insulating layers are subjected to the patterning process so as to expose necessary portions of these electrodes.

In each of the plates, patterns for many sensors can be formed simultaneously on a large substrate by utilizing one of the semiconductor manufacturing techniques, that is, photolithography, so that the sensor according to the present invention is suitable for mass production. The pH-electrode is constituted by depositing a metal oxide film serving as the pH sensitive membrane on a metal electrode or patterned conductive layer, so that it can be formed as a thin film. Thus, the pH-electrode can be formed on the substrate as a thin film pattern, whereby the sensor can be assembled easily.

The sensor is constituted by laminating the above-described plates, and so the electrolyte solution or gel is accommodated in the compartment formed in the flat plate for the pH-electrode which is sandwiched by other plates. Thus, the capacity of the compartment can be made larger by increasing the thickness of the substrate for the pH-electrode or the like, whereby the amount or capacity of the electrolyte to be accommodated in the compartment can be increased, thereby making it possible to extend the lifetime of the carbonic acid gas sensor.

In the carbonic acid gas sensor, the metal oxide film serving as the pH sensitive membrane is formed by an indium oxide or titanium oxide or an oxide film of platinum group metal such as palladium oxide, iridium oxide or platinum oxide so that a low impedance electrode can be provided. Further, noise included in the output of the sensor can be decreased so the a measuring circuit for the sensor can be simplified.

The carbonic acid gas sensor is further provided with a groove for accommodating the electrolyte solution or gel on the pH-electrode, whereby the amount of the electrolyte on the pH-electrode can be made very small. Thus, the change rate of the pH of the electrolyte on the pH-electrode due to the carbonic acid gas diffused through the gas permeable membrane can be made fast. Further, since the distance between the gas permeable membrane and the pH-electrode is determined by the thickness of the insulating layer or a coating film constituting the groove, the distance can be reproduced without fluctuating at every sensor. Thus, the carbonic acid gas sensor has an output characteristic, and in particular, a response time which does not fluctuate at every sensor. Further, since the coating film is a thin film, the pH-electrode can be disposed close to the gas permeable membrane, so that the response time can be made very short.

In the carbonic acid gas sensor, since an effective area of the pH-electrode can be made smaller than that of the gas permeable membrane, the area of the electrolyte in the groove contacting with the gas permeable membrane can be made larger than that contacting with the pH-electrode. Therefore, the amount of the electrolyte which pH is changed by the carbonic acid gas diffused through the gas permeable membrane can be made larger than the amount of the electrolyte on the pH-electrode. Thus, the pH of the electrolyte in the vicinity of the pH-electrode can be changed in the same manner as that of the electrolyte on the pH-electrode, so that a substantial change rate of the pH is held on the pH-electrode even if the electrolyte flows on the groove. Thereby the response characteristic of the sensor can be stabilized.

The area where the electrolyte exists is determined by the groove formed in the coating film provided on the surface of the substrate of the pH-electrode, whereby a good response of the pH for the measurement can be performed.

Furthermore, the pH-electrode and the reference electrode are extracted by lead wires to the rear surfaces of the plates for the pH-electrode and the reference electrode through holes formed in these plates, respectively, and then wired on the rear surfaces thereof to thereby connect the carbonic acid gas sensor to an external measuring circuit. Thus, since output terminals of the sensor can be provided on the surface of the plate opposite to the surface contacting with the solution or gel to be measured, it is possible to protect the connecting portions of the sensor from the solution or gel to be measured.

A carbonic acid gas sensor according to an embodiment of the present invention will hereinafter be described with reference to FIGS. 1 through 7.

FIG. 1 shows a schematic perspective view of the carbonic acid gas sensor according to the embodiment.

Referring to FIG. 1, a carbonic acid gas sensor 1 of a chip-like configuration according to one embodiment of the present invention has a laminated structure. The sensor 1 of the laminated structure is constituted by four layers, that is, from the upper side in FIG. 1, an outer plate 2 in which a gas permeable membrane 7 is formed, a plate 3 for a pH-electrode, an intermediate plate 4, and a plate 5 for a reference electrode. In the plate 3 for the pH-electrode, a pH-electrode serving as a conductor connected to a pH sensitive membrane is formed on an insulating substrate by patterning with gold or platinum. The intermediate plate 4 has cavities for accommodating and holding an electrolyte. In the plate 5 for the reference electrode, a reference electrode is formed on an insulating substrate by patterning with silver/chloride (Ag/AgCl) such that chloride is formed on the major surface of the substrate.

Figure 2:
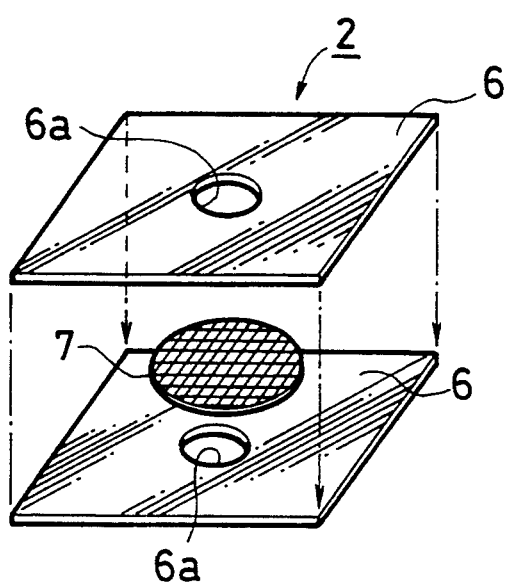
FIG. 2 is an exploded perspective view of an outer plate of the gas sensor shown in FIG. 1.

As shown in FIG. 2, the outer plate 2 is formed by bonding the gas permeable membrane 7 of polytetrafluoroethylene with a thickness of 18 $\mu$m, for example, to a rectangular glass substrate 6 having a through hole 6a at a center thereof in a manner that the through hole 6a is covered by the gas permeable membrane 7 to thereby form a carbonic acid gas permeable window.

Figure 3:
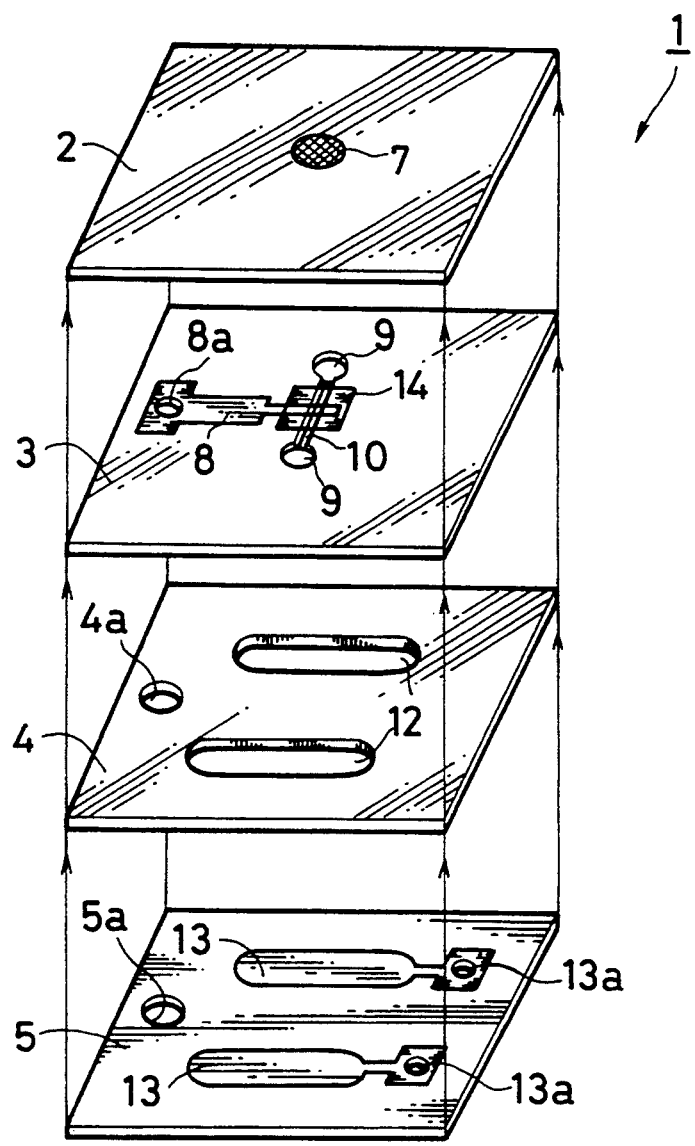
FIG. 3 is an exploded perspective view of the carbonic acid gas sensor shown in FIG. 1.

Referring to FIG. 3, arrows among the respective plates show positional relations among the plates in a case of assembling the sensor.

The outer plate 2 is disposed at the outermost portion of the sensor so that the carbonic acid gas permeable window contacts with a sample to be detected.

Figure 4:
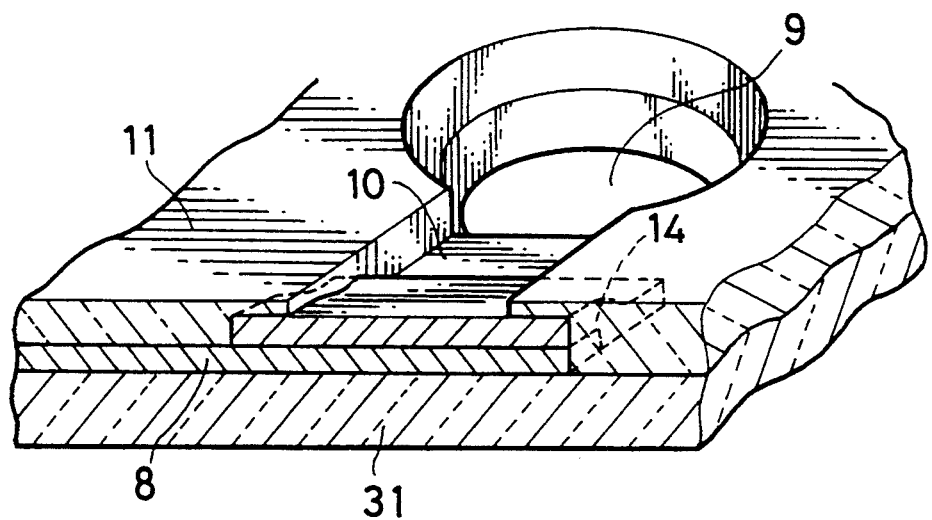
FIG. 4 is a sectional perspective view illustrating a portion around a sensing layer of a plate for a pH-electrode of the gas sensor shown in FIG. 1.

The plate 3 for the pH-electrode positioned adjacent to the outer plate 2 has a conductive layer 8 and the pH sensitive membrane 14 formed on a glass substrate 31 by the patterning process, as shown in FIG. 4. The conductive layer 8 of the pH-electrode is formed by platinum and the pH sensitive membrane 14 is formed by palladium oxide.

The plate 3 for the pH-electrode is provided with two through holes 9 at approximately symmetrical positions with respect to the pH sensitive membrane 14. Referring to FIG. 4, a coating film 11 of polyimide resin is deposited on the surface of the glass substrate 31 on which the pH-electrode is formed. A groove 10 with a predetermined depth of 10 $\mu$m, for example, and a predetermined width is formed on the glass substrate 31 in the patterning process of the coating film 11 so that the pH sensitive membrane 14 is partially exposed in the groove 10. The groove 10 and the through holes 9 form a compartment for accommodating the electrolyte, whereby the exposed portion of the pH sensitive membrane 14 contacts with the electrolyte.

This embodiment employs a solution including NaHCO$_3$ of 10 mM and NaCl of 100 mM, for example, as the electrolyte. The concentration of the NaCl is not limited to this value and may be a voluntary value. The groove 10 is formed so as to extend in a direction perpendicular to the longitudinal direction of the conductor 8 for the pH electrode, so that the conductor 8 can be easily connected to a lead wire for extracting a pH detection signal, that is, a signal representing a detected pH. The electrolyte in the compartment is prevented from leaking out of the compartment by the coating film 11 of the polyimide resin.

When all the plates 2 to 5 are assembled, the exposed portion of the pH sensitive membrane 14 is positioned so as to oppose to the carbonic acid gas permeable window of the outer plate 2. The pH sensitive membrane 14 exposed by partially removing the insulating coating film 11 detects changes in the pH of the electrolyte within the groove 10.

The exposed portion of the pH sensitive membrane 14 within the groove 10 is covered by the electrolyte, and further an area of the exposed portion of the pH sensitive membrane 14 is made smaller than that of the gas permeable window of the outer plate 2. Thus, the amount of the electrolyte whose pH is changed by a carbonic acid gas diffused through the gas permeable membrane 7 can be made larger than that of the electrolyte on the pH-electrode. Accordingly, the change in a pH of the electrolyte on the pH-electrode can be detected stably, so that the sensing ability of the carbonic acid gas sensor can be improved.

The lifetime of the carbonic acid gas sensor will be explained. The amount or capacity of the electrolyte accommodated in the gas sensor, that is, the capacity of the electrolyte is an important factor for determining the life of the carbonic acid gas sensor. A capacity of the electrolyte is determined by the amount of decrease of the electrolyte due to the evaporation of the electrolyte passing out of the sensor through the gas permeable membrane, and also by the amount of the electrolyte which is coagulated as NaCl. The larger the capacity of the electrolyte, the longer the lifetime of the carbonic acid gas sensor.

According to this embodiment, the capacity of the electrolyte can be made quite large by the provision of the intermediate plate 4. Particularly, the intermediate plate 4 is formed by a glass substrate which is provided with a pair of elongated holes 12 for accommodating the electrolyte therein. Each of the holes 12 has an opening whose area is larger than that of the hole 9 of the pH-electrode 3. When the respective plates 2 to 5 are laminated to constitute the sensor, the holes 12 form a cavity for accommodating the electrolyte together with the plates 3 and 5 disposed at opposite sides of the plate 4. The capacity of the electrolyte can be voluntarily set by adjusting the opening areas of the holes 12 and the thickness of the intermediate plate 4.

When the carbonic acid gas sensor according to the present invention is not provided with the intermediate plate 4, in order to increase the capacity of the electrolyte, the opening area of each of the holes 9 formed in the plate for the pH-electrode is increased or the thickness of the substrate 31 of the plate for the pH-electrode is increased.

Referring to FIG. 3, the plate for the reference electrode 5 is disposed at the undermost portion of the sensor. In the plate 5 for the reference electrode, a pair of the reference electrodes 13 are formed on an insulation substrate so as to oppose to the holes 12 of the intermediate plate 4, respectively. The reference electrodes 13 are Ag/AgCl electrodes which are fabricated by forming chloride on silver, and the electrodes 13 form a pair of electrodes for detecting change of pH of the electrolyte together with the pH-electrode. The pair of the reference electrodes 13 communicate with the pairs of the holes 9 and 2 through the electrolyte. On the surface of the plate 5 on which the reference electrodes 13 are formed, an insulating layer may be formed which is subjected to the patterning process so as to expose portions necessary for detecting the change of pH.

The plates 3 to 5 have through holes for extracting lead wires therethrough at connecting portions thereof. Namely, the plate 3 for the pH-electrode is provided with a through hole 8a at the connecting portion, that is, one end portion of the conductive layer 8. The intermediate plate 4 is provided with a through hole 4a for passing the lead wire from the pH-electrode to the rear surface of plate 4. Further, the plate 5 for the reference electrode is provided with through holes 13a at connecting portions, that is, one ends of the reference electrodes 13 and a through hole 5a for passing the lead wire from the pH-electrode to the rear surface of the plate 5. The lead wires of the carbonic acid gas sensor 1 are extracted out of the plate 5 through these through holes.

The respective plates constituting the carbonic acid gas sensor are combined by a bonding agent such as epoxy resin or low fusing point glass. In the bonding process, the bonding agent is pasted on the plates in predetermined patterns by the screen printing method, and then the respective plates 2 to 5 are stacked together unitedly. Then, the stacked plates are sintered or hardened by heat, thereby forming the carbonic acid gas sensor 1.

While an explanation has been made about a method of fabricating a single carbonic acid gas sensor 1 so as to simplify the explanation, in fact, many carbonic acid gas sensors 1 are fabricated simultaneously by utilizing semiconductor manufacturing techniques. Namely, each of the plates 2 to 5 of the above-described carbonic acid gas sensor 1 shown in FIG. 1 etc. constitutes one unit or constituent element of the carbonic acid gas sensor 1. Then, there are prepared a first substrate member having many units of the plates 2 having the gas permeable membranes, a second substrate member having many units of the plates 3 for the pH-electrodes, a third substrate member having many units of the intermediate plates 4, and a fourth substrate member having many units of the plates 5 for the reference electrodes. These first to fourth substrate members are laminated and stacked together in the above-described manner, then the laminated members including many carbonic acid gas sensors are cut so as to cut out many carbonic acid gas sensors 1.

Figure 7:
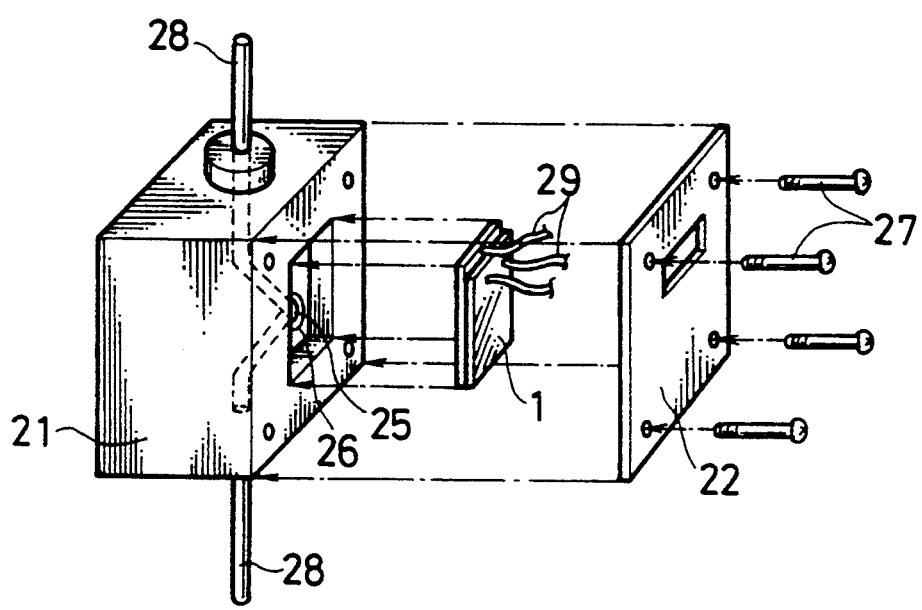
FIG. 7 is an exploded perspective view of a flow cell in which the carbonic acid gas sensor of the present invention is incorporated.

FIG. 7 shows the construction of a flow cell incorporating the sensor of the present invention. A small tube 28 runs through a sensor housing 21. In the housing 21, the tube 28 has a bend with an opening 25 through the tube wall, in a rectangular recess in the wall of the housing 21. The sensor 1 constituted as described above fits into the rectangular recess and its gas permeable window is sealed against the opening 25 by an O-ring 26. A flat cover plate 22 is fastened to the housing 21, e.g., by screws 27, thereby holding the sensor 1 into the recess. The electric leads 29 from the sensor 1 pass out through a small aperture in the cover Liquid flowing in the tube 28 is therefore exposed at the gas permeable membrane 7 of the sensor as it flows past the opening 25, while the O-ring 26 prevents leakage.

Figure 5:
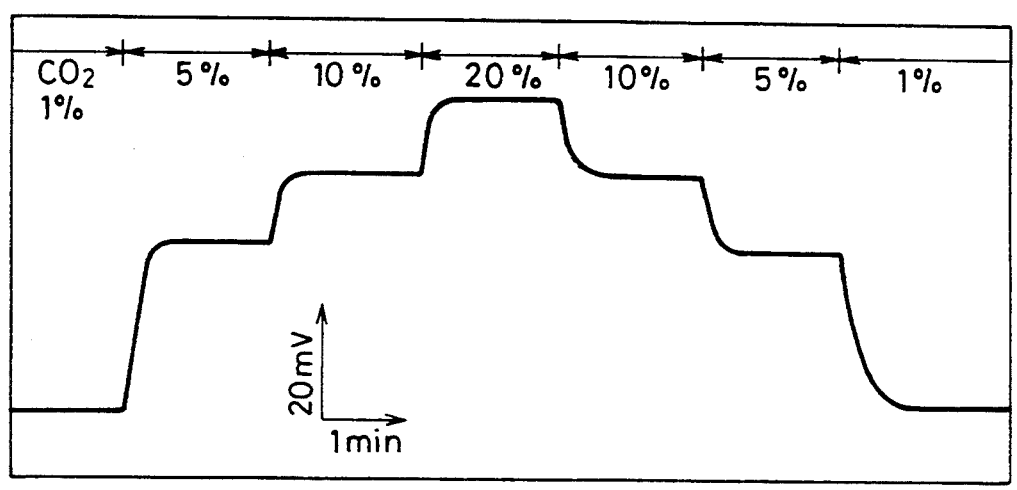
FIG. 5 is a schematic diagram illustrating an example of a time response characteristic of the carbonic acid gas sensor shown in FIG. 1.

FIG. 5 shows an example of a time response characteristic of the carbonic acid gas sensor according to the present invention. In this example, plural samples of water solution, in which carbonic acid gas is dissolved at different concentrations, are subjected to the bubbling process by plural gases which are prepared by mixing carbonic acid gases of different partial pressures in nitrogen gas, respectively. The partial pressures of the dissolved carbonic acid gas of the thus prepared plural samples of the water solution are 1%, 5%, 10% and 20%, for example. These samples of the water solution are sequentially accommodated in the carbonic acid sensor 1, and a voltage difference between the pH-electrode and the reference electrodes 13 is measured at every sample to detect a response time of the sensor 1. A response time differs depending on the partial pressure of the carbonic acid gas of the sample. The latest response time was obtained when a sample with a partial pressure of 5% is replaced with one of 1%. However, the longest response time in this case is still a high speed of 30 seconds.

Figure 6:
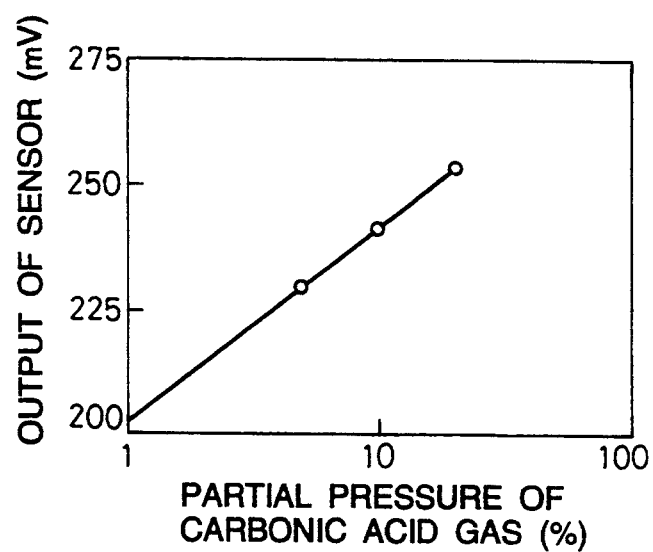
FIG. 6 is a schematic diagram illustrating a calibration curve of the carbonic acid gas sensor of FIG. 1.

FIG. 6 shows a calibration curve representing a relation between output voltages of the carbonic acid gas sensor 1 and the respective partial pressures of the carbonic acid gas. As is clear from FIG. 6, the response time characteristic exhibits a good linearity in the partial pressure range of the carbonic acid gas of 1 to 20%. The sensitivity of the carbonic acid gas sensor in this example is 52 mV/decade.

Having described the preferred embodiment of the invention with reference to the accompanying drawings, it is to be understood that the invention is not limited to this precise embodiment and that various modifications thereof could be effected by one skilled in the art without departing from the spirit or scope of the invention as defined in the appended claims.

What is claimed is:

1. A carbonic acid gas sensor capable of detecting carbonic acid gas dissolved in fluid, comprising:
   an outer plate including first and second glass substrates each having a window formed therein and fixedly sandwiching a gas permeable membrane to form a carbonic acid gas permeable window;

a first supporting plate supporting a pH-electrode, for detecting a pH of an electrolyte, including an insulating substrate, a pH sensitive membrane formed on said substrate so as to oppose said carbonic acid gas permeable window, and a compartment for accommodating the electrolyte, said compartment extending through the thickness of said first supporting plate; and a second supporting plate supporting a reference electrode, wherein said outer plate, said first supporting plate and said second supporting plate are laminated.

2. A carbonic acid gas sensor according to claim 1, wherein said pH sensitive membrane is formed by an oxide of a platinum group metal.

3. A carbonic acid gas sensor according to claim 2, wherein said oxide is a palladium oxide.

4. A carbonic acid gas sensor according to claim 2, wherein said oxide is an iridium oxide.

5. A carbonic acid gas sensor according to claim 2, wherein said oxide is a platinum oxide.

6. A carbonic acid gas sensor according to claim 1, wherein said pH sensitive membrane is an indium oxide membrane.

7. A carbonic acid gas sensor according to claim 1, wherein said first supporting plate further includes a conductive layer formed on said insulating substrate and to be connected to an external lead wire, and said pH sensitive membrane is disposed on said conductive layer so as to cover a part thereof.

8. A carbonic acid gas sensor according to claim 7, wherein each of said first supporting plate and said second supporting plate has a through hole for wiring, and the lead wire connected to said conductive layer is extracted out of said second supporting plate through said through holes.

9. A carbonic acid gas sensor according to claim 1, wherein said pH sensitive membrane contacts with the electrolyte in said compartment.

10. A carbonic acid gas sensor according to claim 1, wherein said compartment of said first supporting plate includes a hole formed in said insulating substrate and a groove formed at a part of a composite resin layer covering the surface of said insulating substrate, and said groove communicates with said hole.

11. A carbonic acid gas sensor according to claim 1, further comprising an intermediate plate having a cavity for accommodating the electrolyte and disposed between said first supporting plate and said second supporting plate.

12. A carbonic acid gas sensor according to claim 1, wherein an exposed area of said pH sensitive membrane is smaller than an area of said carbonic acid gas permeable window.

* * * * *